United States Patent [19]

Heldreth et al.

[11] Patent Number: 5,129,907
[45] Date of Patent: Jul. 14, 1992

[54] PATELLAR CLAMP AND REAMER WITH ADJUSTABLE STOP

[75] Inventors: Mark A. Heldreth, Mentone; Cary R. Reeves, Leesburg, both of Ind.

[73] Assignee: Zimmer, Inc., Warsaw, Ind.

[21] Appl. No.: 625,253

[22] Filed: Dec. 10, 1990

[51] Int. Cl.$^5$ .............................................. H61F 5/04
[52] U.S. Cl. ......................................... 606/80; 606/88
[58] Field of Search ................ 408/14, 241 S; 606/79, 606/80, 81, 86, 87, 88, 96, 99, 102; 623/16, 39

[56] References Cited

U.S. PATENT DOCUMENTS

| | | | |
|---|---|---|---|
| D. 273,326 | 4/1984 | Peterson et al. | D24/27 |
| 2,291,413 | 7/1942 | Siebrandt | 606/86 |
| 2,427,128 | 9/1947 | Ettinger | 128/346 |
| 2,698,483 | 1/1955 | Berkowitz | 32/63 |
| 3,037,405 | 6/1962 | Steyskal | 408/241 S |
| 3,126,767 | 3/1964 | Sawyer | 408/14 |
| 3,724,963 | 4/1973 | Stadtmiller | 408/14 |
| 3,979,165 | 9/1976 | Pyle | 408/14 |
| 4,312,337 | 1/1982 | Donohue | 128/92 EB |
| 4,444,180 | 4/1984 | Schneider et al. | 128/92 EB |
| 4,565,192 | 1/1986 | Shapiro | 128/92 H |
| 4,586,497 | 5/1986 | Dapra et al. | 128/92 E |
| 4,633,862 | 1/1987 | Petersen | 606/80 |
| 4,706,660 | 11/1987 | Petersen | 606/80 X |
| 4,736,737 | 4/1988 | Fargie et al. | 606/88 |
| 4,750,481 | 6/1988 | Reese | 606/87 |
| 4,952,213 | 8/1990 | Bowman et al. | 606/79 |
| 5,002,547 | 3/1991 | Poggie et al. | 606/88 |
| 5,021,055 | 6/1991 | Burkinshaw | 606/82 |

OTHER PUBLICATIONS

Biomet Inc. AGC-Total Knee system: Patellar Instrumentation, 1990.
Depuy-AMK Total Knee System Design Rationale and Surgical Procedure-Engh et al.-3 pages including p. 25.
Dow Corning Wright-Whiteside Ortholoc II Total Knee System: Surgical Technique Patella Recessing-pp. 1-5.
Dow Corning Wright-"We're Pushing All the Wright Buttons".
Intermedics Orthopedics, Inc.-The Intermedics Natural-Knee System-Hoffman-pp. 23-24.
Richards-pp. 37-38-Various Patellar Instruments.
Richards-Tricon-M (Knee) With Pro-Fit Surgical Procedures-4 pages including pp. 14-15.
Richards-Genesis Total Knee System: Addressing the Unexpected-Cruciate-Retaining Primary Technique-pp. 21-23,24.

Primary Examiner—Robert A. Hafer
Assistant Examiner—Brian E. Hanlon
Attorney, Agent, or Firm—Margaret L. Geringer

[57] ABSTRACT

A patellar clamp and reamer for performing either a total surfacing procedure or insetting procedure for preparing the patellar surface for a prosthetic implant, including an adjustable stop connected to the clamp and engaging a collar on the reamer shaft to space the reamer blade a calibrated distance from the clamp's reference jaw. The stop is calibrated and includes indicia thereon in terms of the thickness of patellar bone to remain after resection.

8 Claims, 4 Drawing Sheets 5,129,907

PATELLAR CLAMP AND REAMER WITH ADJUSTABLE STOP

FIELD OF THE INVENTION

This invention relates to a patellar clamp and reamer and has specific relevance to a patellar clamp and reamer having an adjustable stop.

BACKGROUND OF THE INVENTION

A patellar clamp and reamer is used during a total knee arthroplasty procedure to prepare the posterior surface of a patellar bone to accept a prosthetic implant. A description of such a patella reamer may be had by reference to U.S. patent application Ser. No. 464,028 filed Jan. 12, 1990, incorporated herein by reference. As described in the incorporated application, the patella is clamped between a fixed jaw and a shiftable guide. The guide provides alignment for a shaft and blade to help avoid malalignment due to tilting during resection on the posterior surface of the patella. The guide, shaft and blade come in a plurality of sizes to accommodate a variety of patella sizes.

Typically, a surgeon will select to install a patellar prosthesis either by utilizing a surfacing technique wherein the prosthetic patella will be positioned on the prepared surface of the patella or by an insetting technique wherein the prosthetic patella will be recessed or inset into the prepared surface of the patella. Accordingly, two varieties of guides could be available for connection to the patellar clamp and could be interchangeably connectable to the clamp. The interchangeable guides permit a surgeon to use the patellar clamp during either a total patellar bone surfacing procedure or a patella insetting procedure.

In either a total resurfacing procedure or a patella insetting procedure, it is important that a sufficient amount of bone stock remain after resection to accept the fixation pegs of the patellar prosthesis and maintain the integrity of the remaining patellar bone. There may be some debate on the exact amount of patellar bone material that should be left after resection. At least one teaching requires that at least 11 millimeters (mm) should remain of the patellar bone stock after resection. For the purpose of this discussion it is assumed that 11 mm of bone stock should remain after resection. If too much bone material is removed, the remaining patellar bone may be structurally weak.

In order to prevent an excessive amount of bone material from being resected a prior art clamp and reamer included a stop ring carried by the shaft above the reamer blades. This type of stop controls the amount of bone removed from the patella, but does not control the minimum thickness of patella bone remaining. The stop ring engages with the upper surface of the reamer guide to stop the shaft and reamer from being further shifted into the patellar bone. A plurality of stop rings having a plurality of effective thicknesses may be interchangeably connected to the shaft of the reamer to accommodate the varying amount of bone to be resected as the thickness of the patellar bone varies between patients. The stop rings may be calibrated and may include measurement indicia thereon, in terms of the amount of bone material to be removed during resection. For example, if a surgeon needs to resect 10 mm of bone material, a ringed stop having the indication 10 mm, and correspondingly an effective thickness of 10 mm, would be turned onto the shaft. Therefore, the shaft and reamer would only be able to resect 10 mm of bone material before the ring stop engages the guide.

SUMMARY OF THE INVENTION

The patellar clamp and reamer of this invention enhances the prior art clamp and stop rings described above by providing an adjustable depth gauge wing carried by the clamp and engaged by a collar on the reamer shaft. The engagement of the collar and depth gauge wing prevents further movement of the reamer into the patella. The adjustable depth gauge wing includes a stepped upper surface having measurement indicia thereon which refers to distance in terms of the amount of patellar bone material to be left after resection. The depth gauge wing is formed from a arcuate plate rotatably connected to the clamp in a generally horizontal plane a fixed distance from the rigid lower jaw of the clamp. The upper surface of the wing is stepped in an ascending manner. The lowest level of the depth gauge wing of the preferred embodiment is marked by the numeral 11 and is of a thickness such that as the collar on the reamer shaft contacts level 11, the blade carried by the shaft is 11 mm from the lower jaw. The 11 mm spacing between blade and lower jaw when the collar abuts level 11 on the depth gauge wing directly correlates to 11 mm of bone material remaining after resection. Therefore, a surgeon using the clamp and reamer of this invention will be assured that when the collar contacts level 11 of the depth gauge wing that 11 mm of bone material remain. If the surgeon desires more than 11 mm of bone material to remain after resection, the depth gauge wing may be rotated until one of its graduated stepped levels is positioned to contact the collar on the shaft. In the preferred embodiment, after the minimum level of 11, each stepped level is 2 mm greater than the lower proceeding level, providing levels 12, 14, and 16. The depth gauge wing is connected to the clamp such that it cannot be deactivated. Therefore, using the clamp and reamer of this invention, the minimum amount of bone material remaining after resection will always be at least 11 mm. This is consistent with the desired amount of bone material that should remain after resection as previously described.

Accordingly, it is an object of this invention to provide a novel patellar clamp and reamer having an adjustable depth stop wing.

Another object of the invention is to provide a patellar clamp and reamer wherein the depth stop wing is calibrated in terms of the amount of bone material to be left after resection of the posterior patellar surface.

Still another object of the invention is to provide a stop for a patellar clamp and reamer having a plurality of stepped levels.

Still other objects of the invention will become apparent upon a reading of the following description taken with the accompanying drawings.

BRIEF DESCRIPTION OF THE DRAWINGS

FIG. 7 is a perspective view of the depth gauge wing removed from the clamp.

DESCRIPTION OF THE PREFERRED EMBODIMENT

Figure 1:
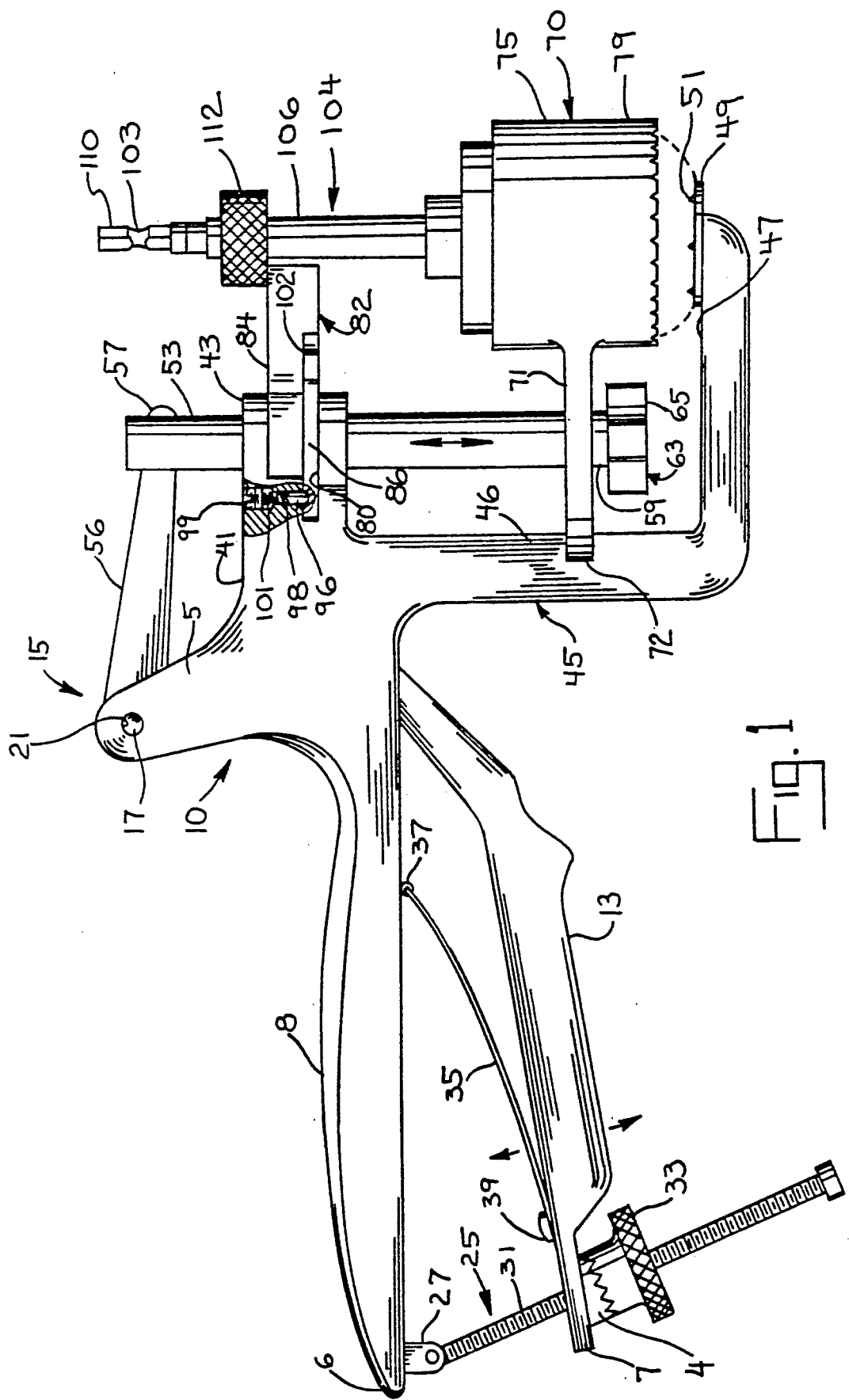
FIG. 1 is a side elevational view of the patellar clamp and reamer of this invention with a patellar bone shown in broken lines for illustrative purposes. A surfacing guide as used in a total patella surfacing procedure is illustrated. Portions of the clamp are cut away for illustrative purposes.
Figure 2:
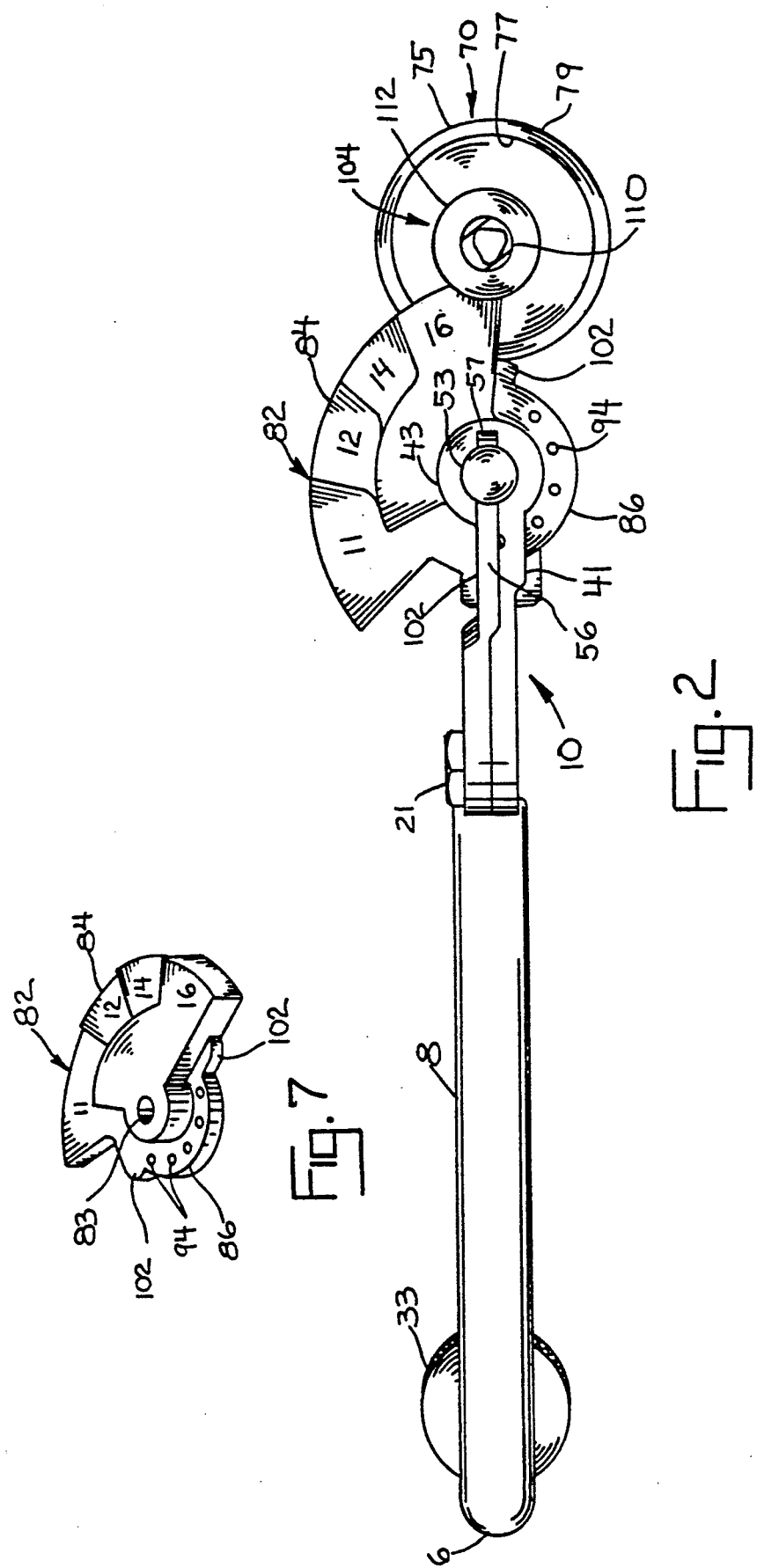
FIG. 2 is a top elevational view of FIG. 1.
Figure 3:
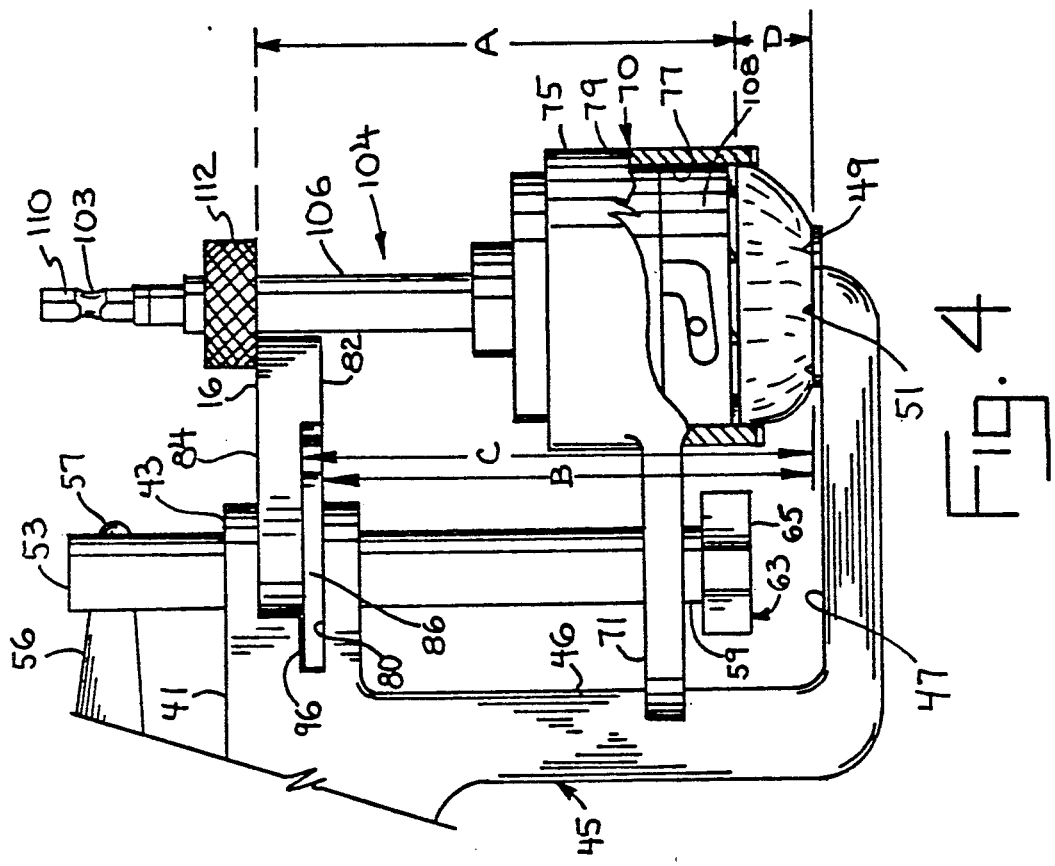
FIG. 3 is a fragmented view of FIG. 1 with the reamer shaft and blade contacting the posterior surface of the patellar bone prior to resection. Portions of the surfacing guide are cut away for illustrative purposes.

The preferred embodiment herein described is not intended to be exhaustive or to limit the application to the precise form disclosed. Rather, it is chosen and described in order to best explain the invention so that others skilled in the art can utilize its teachings.

With reference to the figures, a patellar clamp-guide device is generally designated by the reference numeral 10 and is seen to include a first handle 8 and a second handle 13. Handles 8 and 13 are attached together at a fulcrum 15 by virtue of a bolt 17 extending through an opening (not shown) in the handle 13 and opening 21 in handle 8.

A locking device 25 is mounted on a proximal end 6 of the handle 8 at a pivoting connection 27 and extends through an opening formed in a proximal end 7 of the handle 13. The locking device 25 includes a threaded rod 31 extending through the opening in handle 13 as described above and having a threaded fastener 33 threaded thereover and engageable with an outside surface 4 of the handle 13 to lock the position of the handles 8 and 13 with respect to one another as desired. A leaf spring 35 slidably engages the handle 8 at 37 and is fastened to the handle 13 preferably by fastening devices such as a screw 39 shown in FIG. 1.

The distal end of the handle 8 includes a projecting portion 5 in which the opening 21 is formed. The distal end of handle 8 also includes an extension 41 carrying a guiding sleeve 43 and an L-shaped jaw 45 terminating at a flat surface 47 on which is mounted a patella engaging plate 49. Plate 49 includes a plurality of upstanding spikes 51 designed to enter the anterior surface of the patella (shown in broken lines only in FIG. 1).

The guiding sleeve 43 is designed to guidingly receive a plunger 53 having a slot therethrough at one end thereof designed to receive a protrusion 57 forming a termination of an elongated portion 56 of the handle 13 distal of the fulcrum 15. Thus, movement of the handle 13 with respect to the handle 8 causes reciprocatory movement of the plunger 53 within the guiding sleeve 43. The plunger device 53 has an end 59 which includes a blind threaded bore sized to receive the threaded end of a locking fastener 63. Locking fastener 63 includes a head 65 designed to be gripped by the user so that the locking fastener 63 may be rotated in one or the other direction. A more thorough explanation of the basic operation of the patellar clamp 10 may be had by reference to the incorporated patent application.

A surfacing reamer guide 70, or insetting reamer guide 90, is detachably connected to the plunger 53 by virtue of the locking fastener 63. The reamer guide 70 or 90 includes an attachment portion 71 having an elongated slot therein, and a guide portion 75 having a central guiding opening 77 as well as an outer periphery 79 substantially concentric thereto. The locking fastener 63 allows different sized reamer guides 70 to be assembled to the plunger 53 to fit different sized patellae. A guide structure 46 is provided which may be engaged with the proximal end 72 of the reamer attachment portion slot (not shown) to provide guidance to the reamer guide in its reciprocatory movements along with the plunger 53.

A lateral notch 80 is formed through guiding sleeve 43 of handle 8. A depth gauge wing 82 having a stepped depth gauge portion 84 and an arcuate detent flange 86 is positioned so that flange 86 is shiftably received within notch 80. Wing 82 is rotatably connected to sleeve 43 by the accommodation of plunger 53 through bore 83 of wing 82. The radius of depth gauge portion 84 is greater than the radius of flange 86 therefore depth gauge 84 extends outwardly in a plane from sleeve 43. The bottom surface of wing 82 is smooth or flat. The upper surface of depth gauge portion 84 is stepped in graduated increments to define levels 11, 12, 14 and 16 in the preferred embodiment. A plurality of dimples 94 are formed in the upper surface of flange 86. A detent 96, housed within a bore 98 of handle 8, engages dimples 94 of detent flange 86 as the wing 82 is rotated. A helical spring 101 carried within bore 98 urges the detent 96 into contact with detent flange 86. The spring 101 and detent 96 are retained within bore 98 by screw 99 and contact with flange 86 of wing 82. The biased seating engagement between detent 96 and dimples 94 provides a positive positioning of the depth gauge wing 82 as it is rotated about plunger 53. A shoulder 102 is formed at each radial end of detent flange 86 adjacent the depth gauge portion 84 of wing 82. Shoulders 102 abut against the side walls of extension 41 adjacent notch 80 to define the rotational limits of wing 82 relative to handle 8.

Figure 4:
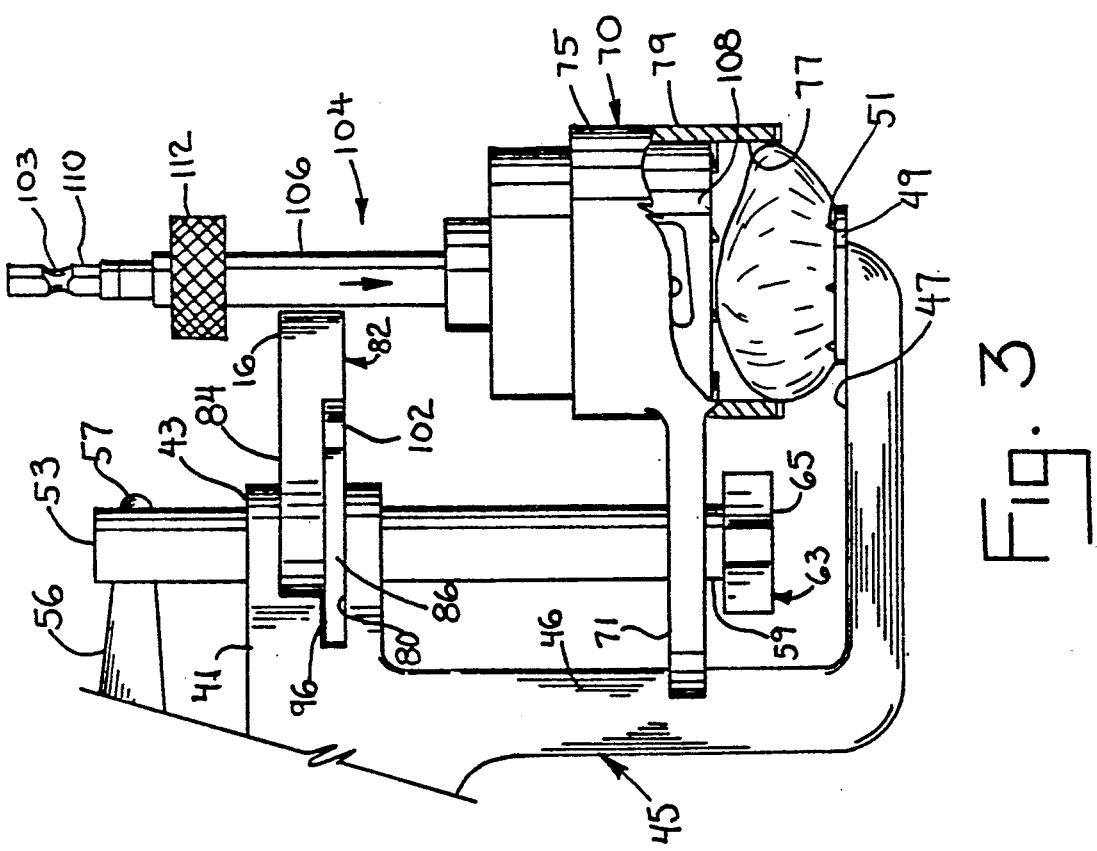
FIG. 4 is a continuation of FIG. 3 with the bone material fully resected and the shaft collar engaging the depth gauge wing.

A reaming cutting device 104 having a shaft 106 and removable blade 108 is provided and includes a chuck 110 having an annular recess 103 adapted to couple with an annular protrusion formed on the interior surfaces of a coupling device for a rotary instrument (not shown). Shaft 106 further includes an annular collar 112. With the chuck 110 coupled to the rotary instrument (not shown), the reaming cutting device 104 may be rotated so that reaming operations may be carried out. Cutting device 104 is constructed such that the distance A between the bottom wall of the cutter and the lower surface of collar 112 is a predetermined and fixed distance (see FIG. 4). Similarly, the distance B between the bottom surface of depth gauge wing 82 and the upper surface of plate 49 is also a predetermined and fixed distance. The distance C from the upper stepped surface of clamp wing 82 to the plate 49 varies as depth gauge wing 82 is rotated about plunger 53. As wing 82 is rotated, distance C varies which correspondingly varies the distance D between the bottom of the blade 108 and plate 49. Therefor, if wing 82 is rotated such that level 11 is aligned with the shaft 106 of cutting device 104, the blade 108 is 11 mm from plate 49 when collar 112 contacts wing 82 at level 11. A surgeon can therefore set the wing 82 in terms of the amount of bone material to remain after resection regardless of the initial thickness of the patella.

Figure 5:
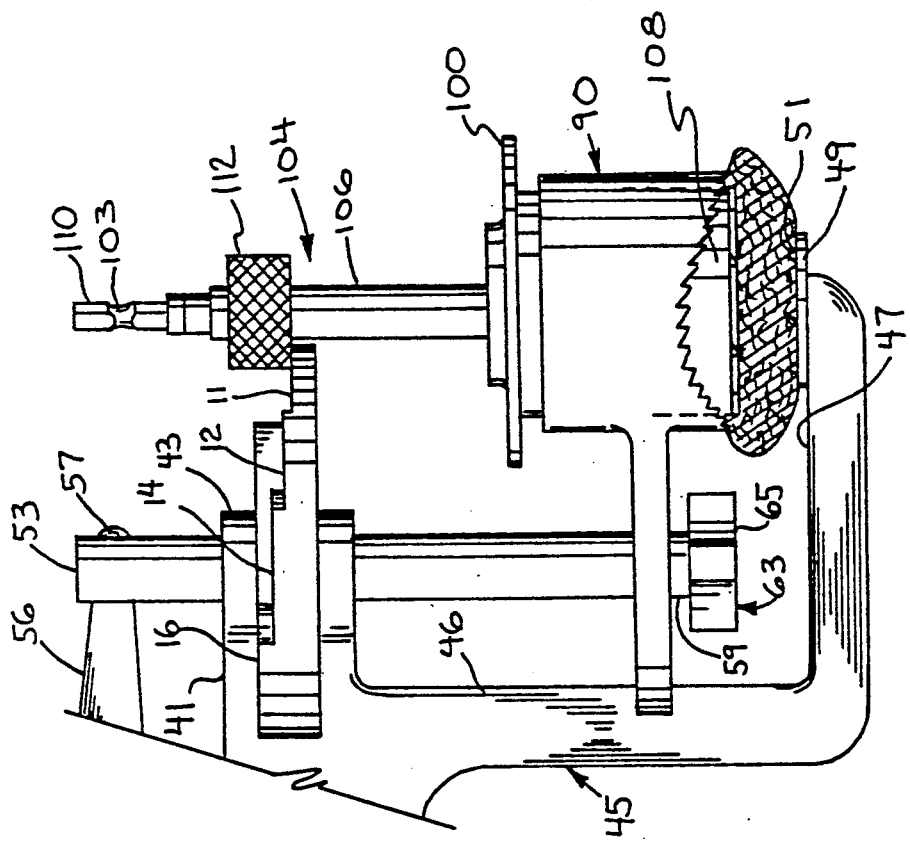
FIG. 5 is a fragmented side elevational view of the patellar clamp and reamer of the invention. An insetting guide is shown in clamping engagement with a patellar bone. A stop ring is connected to the shaft and is elevated above the insetting guide by the blades contact with the unresected surface.
Figure 6:
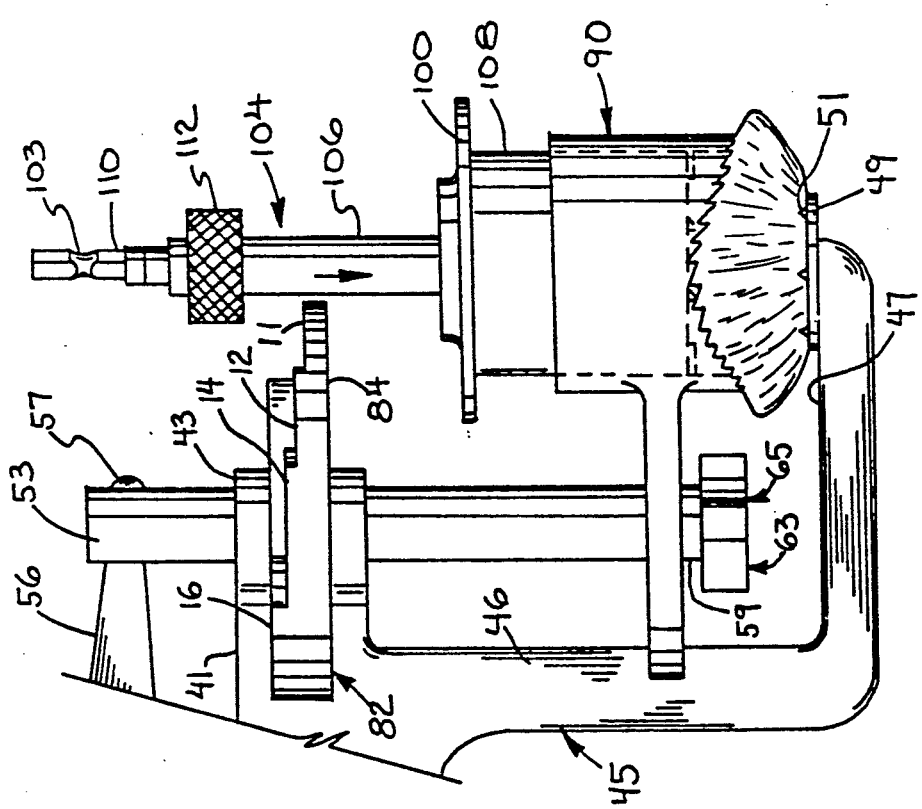
FIG. 6 is a continuation of FIG. 5 with the bone material resected and the shaft collar engaging the depth gauge wing. The stop ring remains slightly elevated above the insetting guide.

In use, a surgeon attaches either a surfacing guide 70 as shown in FIGS. 1-4 or an insetting guide 90 as shown in FIGS. 5 and 6 to patellar clamping device 10. The choice of guide type and size depends on the type of procedure to be performed and the physical size of the patellar bone.

FIGS. 1-4 illustrate the clamping reaming device 10 with a surfacing guide attached thereto and in clamping engagement with a patellar bone. The surgeon using the device in this configuration would measure the thickness of patellar bone and determine in his judgment the amount of bone stock to remain after resection. Depth gauge wing 82 is rotated to position the level corresponding to the amount bone stock to remain in line with the shaft of the reaming cutting device 104. For example, if the surgeon requires 16 mm of bone stock to remain after resection, the depth gauge wing 82 is rotated to position the level designated by the numeral 16 in line with the reaming cutting device shaft as shown in FIGS. 1-4. The detent 96 engages within a dimple 94 to retain the depth gauge wing 82 in position. During resection, when collar 112 contacts the depth gauge wing 82, further resection is prevented and 16 mm of bone stock remains between the bottom of the cutter blade 108 and plate 49.

To perform an insetting procedure, the insetting guide 90 is attached in the same manner as described above with guide 70. The thickness of the patellar bone is measured and the surgeon calculates the amount of patellar bone material to be recessed to accept the patellar prosthetic button (not shown). The surgeon also must consider that after resection of the calculated amount, sufficient patellar bone thickness should remain. A stop ring 100 calibrated in terms of the amount of bone material to be resected may be threaded onto reaming device 104. The particular thickness of stop ring 100 used depends on the amount of bone material to be resected. For example, if the surgeon calculates that 10 mm of bone material should be removed, a stop ring 100 having an effective thickness of 10 mm is turned onto the shaft 106. It is intended that when the 10 mm stop ring contacts the upper surface of the guide 90, 10 mm of bone material has been removed and further progression of the reaming cutting device 104 into the patellar bone is prevented. The surgeon rotates depth gauge wing 82 so as to position a step 11, 12, 14 or 16 in line with the shaft 106. The particular level of the depth gauge wing 82 that is positioned in line with the shaft 106 is determined by the amount of bone material to be left after resection. For example, if after resection the surgeon feels it appropriate to have at a minimum 11 mm of bone material remaining, the depth gauge wing 82 is rotated such that the level identified by numeral 11 is aligned with shaft 106. During resection, the bone material is reamed away by rotation of shaft 106 and blade 108 in a known manner. When collar 112 contacts the depth gauge wing 82 at level 11 the surgeon is assured that 11 mm of patellar bone material remains between the bottom wall of the cutter and plate 49.

Referring to FIGS. 5 and 6, the patellar clamp-reaming device 10 is illustrated in association with insetting guide 90 in the process of performing an insetting procedure on a patella. A stop ring 100 is connected to the reaming cutting device 104 to engage the guide when the required amount of bone material has been recessed. Depth gauge wing 82 has been positioned in the "inset" level designated by numeral 11. As shown in FIG. 6, if during resection, stop ring 100 has not yet engaged the guide 90 before collar 112 engages depth gauge wing 82, the contact between the collar 112 and wing 82 prevents further movement of the reaming cutting device 104 into the patellar bone, ensuring that an 11 mm thickness of bone remains with wing 82 set at level 11. In essence, when the depth gauge wing 82 and reaming cutting device 104 is used in conjunction with a stop ring 100, two separate and distinct depth gauges ensure against excessive accidental bone removal. The stop ring 100 is gauged in terms of bone material to be resected, while the depth gauge wing 82 is gauged in terms of patellar bone stock to remain after resection. The depth gauge wing 82 may be the only stop means used, or, if desired, it may be used in conjunction with a stop ring 100 as shown in FIGS. 5 and 6. If collar 112 contacts wing 82 before stop ring 100 contacts guide 90, as shown in FIG. 6, this would ensure that the desired thickness of bone remains, even though the full 10 mm of bone would thus not be removed. If ring 100 contacts guide 90 first (not shown) this would indicate desired 10 mm of bone was removed, and that at least the desired minimum amount of bone (or greater) still remains.

It should be understood that the particular number of levels on wing 82 as well as the distances represented thereon may be merely one of design choice. Further, that while a rigid, one piece depth gauge wing 82 is illustrated, any number of depth gauge devices may be conceivable to function in the same manner. For example, a plurality of pivotal shims could be used instead of a single shim with stepped upper surface as described above. With the plurality of shims, the user could choose whether to activate one or more shims into position to control the amount of patellar bone to remain. Alternatively, the plurality of shims may not be pivotal, but may be selectively stacked into position, as desired. In addition, a stepped wing could be utilized which is not pivoted into position as described herein, but wherein the stepped wing is slid or otherwise positioned to operatively position the desired thickness of step into position to engage the collar on the reamer shaft. It is understood that these alternatives are in keeping with the scope of the invention as herein presented, such that the stop or shim engages with a collar on the reamer shaft to control the distance between a reference jaw of the clamp/reamer and the cutting surface of the reamer, thus controlling the thickness of patellar bone remaining, and that such stop may be adjustable. The choice of the depth gauge wing shown herein is the preferred embodiment known at the time of the invention.

It should also be understood that the invention is not to be limited to the precise form disclosed but may be modified within the scope of the appended claims.

We claim:

1. In combination, a patellar clamp including a stop and a reaming device, said clamp including at least one jaw part for engagement with a surface of a patella, said reaming device including a shaft having a collar and a cutter, said stop being connected to said clamp above said jaw part and including a spacing means connected to said clamp for engagement with said collar on said reamer shaft for spacing said cutter a predetermined distance above said jaw, and wherein said spacing means includes an upper surface, said upper surface being stepped to include a plurality of levels, said stop being movably connected to said clamp to selectively position one of said levels for engagement with said collar.

2. A patellar clamp having a first jaw and a second jaw held in shiftable association relative to one another for clamping engagement with a patella positioned therebetween, said first jaw constituting a reamer guide and including an opening therethrough for accommodating a reamer, a depth stop means being rigidly connected to said second jaw for engagement with a reamer shaft to space a blade of said reamer a predetermined distance from said second jaw.

3. The patellar clamp of claim 2 wherein said depth stop means is adjustable to vary said predetermined distance.

4. The patellar clamp of claim 2 wherein said depth stop means includes an upper surface having a plurality of stepped levels, such that as said depth stop means is positioned to locate one of said levels for engagement with the reamer shaft, said predetermined distance is varied.

5. The patellar clamp of claim 2 wherein said reamer shaft includes an extending collar for engagement with said depth stop means.

6. The patellar clamp of claim 2 wherein said second jaw includes a first portion positioned on one side of the opening in the reamer guide and a second portion interconnected to said first portion and positioned on the other side of the opening in the reamer guide, and wherein the depth stop means is connected to the first portion of the second jaw for engagement with the reamer shaft to space the blade of the reamer a predetermined distance from the second portion of the second jaw.

7. A patellar clamp having a first jaw and a second jaw held in shiftable association relative to one another for clamping engagement with a patella positioned therebetween, said first jaw constituting a reamer guide and including an opening therethrough for accommodating a reamer, a depth stop means being rigidly connected to one of said first and second jaws for engagement with a reamer shaft to space a blade of said reamer a predetermined distance from the other of said first and second jaws, and wherein said depth stop means includes an upper surface having a plurality of stepped levels, such that as said depth stop means is rotated to position one of said levels for engagement with the reamer shaft, said predetermined distance is varied.

8. A depth stop for a patellar clamp, said depth stop comprising a body having an upper surface including a plurality of graduated levels, a through bore for accommodation of a connection device for connection of said stop to said clamp, said depth stop including a flange about a portion of said bore, said flange including a plurality of dimples for accommodation of a biased plunger therein.

* * * * *

UNITED STATES PATENT AND TRADEMARK OFFICE
CERTIFICATE OF CORRECTION

PATENT NO. : 5,129,907
DATED : July 14, 1992
INVENTOR(S) : Heldreth et al.

It is certified that error appears in the above-identified patent and that said Letters Patent is hereby corrected as shown below:

IN THE TITLE PAGE:

In the inventor section [75], please add "Kim C. Bertin, Bountiful, Utah" as a co-inventor.

Signed and Sealed this

Twenty-eighth Day of September, 1993

Attest:

BRUCE LEHMAN

Attesting Officer  Commissioner of Patents and Trademarks